United States Patent
Kalantzis et al.

(10) Patent No.: US 12,353,966 B2
(45) Date of Patent: Jul. 8, 2025

(54) SPECTRAL CLUSTERING OF HIGH-DIMENSIONAL DATA

(71) Applicant: International Business Machines Corporation, Armonk, NY (US)

(72) Inventors: Vasileios Kalantzis, White Plains, NY (US); Lior Horesh, North Salem, NY (US)

(73) Assignee: International Business Machines Corporation, Armonk, NY (US)

(*) Notice: Subject to any disclaimer, the term of this patent is extended or adjusted under 35 U.S.C. 154(b) by 1020 days.

(21) Appl. No.: 17/384,197

(22) Filed: Jul. 23, 2021

(65) Prior Publication Data

US 2023/0045753 A1  Feb. 9, 2023

(51) Int. Cl.
*G06N 20/00* (2019.01)
*G06F 16/901* (2019.01)
*G16H 50/70* (2018.01)

(52) U.S. Cl.
CPC ......... *G06N 20/00* (2019.01); *G06F 16/9024* (2019.01); *G16H 50/70* (2018.01)

(58) Field of Classification Search
CPC ..... G06N 20/00; G16H 50/70; G06F 16/9024
See application file for complete search history.

(56) References Cited

U.S. PATENT DOCUMENTS

| | | | |
|---|---|---|---|
| 6,711,528 B2 | 3/2004 | Dishman et al. | |
| 6,922,715 B2 | 6/2005 | Kobayashi et al. | |
| 10,839,306 B2 | 11/2020 | Mezzacapo et al. | |
| 2006/0074821 A1* | 4/2006 | Cristianini | G06N 20/00 706/12 |
| 2011/0245622 A1* | 10/2011 | McKenna | G16Z 99/00 600/300 |
| 2018/0189601 A1* | 7/2018 | Dabeer | G06V 20/588 |
| 2018/0241764 A1* | 8/2018 | Nadolski | H04L 63/20 |
| 2019/0114680 A1* | 4/2019 | Chien | G06N 20/00 |

(Continued)

FOREIGN PATENT DOCUMENTS

IN  202011022086 A  6/2020

OTHER PUBLICATIONS

Kalantzis, Vassilis, Yuanzhe Xi, and Lior Horesh. "Fast randomized non-Hermitian eigensolvers based on rational filtering and matrix partitioning." SIAM Journal on Scientific Computing 43.5 (2021): S791-S815. (Year: 2021).*

(Continued)

*Primary Examiner* — Andrew T Chiusano
(74) *Attorney, Agent, or Firm* — Scully, Scott, Murphy & Presser, P.C.; Andre L. Adkins

(57) ABSTRACT

A processor performing machine learning including spectral clustering can receive data from the sensor. Graph Laplacian of the data can be created and stored in a memory device. Spectral characteristic can be created by applying density of states and spectral gaps can be detected in an unsupervised manner in the spectral characteristic to determine r as number of clusters to cluster the data. A range space of a rational matrix of the graph Laplacian can be determined. K-means clustering can be performed on the range space of rational matrix of the graph Laplacian using r as the number of clusters, the K-means clustering returning r clusters of the received data.

6 Claims, 13 Drawing Sheets

(56) References Cited

U.S. PATENT DOCUMENTS

2022/0014554 A1* 1/2022 Vasu ................ H04L 63/102

OTHER PUBLICATIONS

Ng, Andrew, Michael Jordan, and Yair Weiss. "On spectral clustering: Analysis and an algorithm." Advances in neural information processing systems 14 (2001). (Year: 2001).*

Zelnik-Manor, Lihi, and Pietro Perona. "Self-tuning spectral clustering." Advances in neural information processing systems 17 (2004). (Year: 2004).*

Sanguinetti, Guido, Jonathan Laidler, and Neil D. Lawrence. "Automatic determination of the number of clusters using spectral algorithms." 2005 IEEE Workshop on Machine Learning for Signal Processing. IEEE, 2005. (Year: 2005).*

Bach, Francis, and Michael Jordan. "Learning spectral clustering." Advances in neural information processing systems 16 (2003). (Year: 2003).*

Tang, Ping Tak Peter, James Kestyn, and Eric Polizzi. "A new highly parallel non-Hermitian eigensolver." arXiv preprint arXiv: 1404.2891 (2014). (Year: 2014).*

Tremblay, Nicolas, and Andreas Loukas. "Approximating spectral clustering via sampling: a review." Sampling techniques for supervised or unsupervised tasks (2020): 129-183. (Year: 2020).*

Whittaker, C., "7 Innovative Uses of Clustering Algorithms in the Real World", https://datafloq.com/read/7-innovative-uses-of-clustering-algorithms/6224, Apr. 4, 2019, Accessed on Jul. 23, 2021, 4 pages.

Bagarello, F., et al., "Eigenvalues of non-hermitian matrices: a dynamical and an iterative approach", arXiv:2002.05015v1, Feb. 12, 2020, 26 pages.

Ye, X., et al., "A Fast Contour-Integral Eigensolver for Non-Hermitian Matrices", SIAM Journal on Matrix Analysis and Applications, Published online Nov. 2, 2017, 31 pages, vol. 3, Issue No. 4.

Kalantzis, V., et al., "Beyond Automated Multilevel Substructuring: Domain Decomposition With Rational Filtering", SIAM Journal on Scientific Computing, 2018, 26 pages, vol. 40, Issue No. 4.

Beyn, W.-J., "An integral method for solving nonlinear eigenvalue problems", Linear Algebra and its Applications (2012), Accepted Mar. 15, 2011, Available online Apr. 20, 2011, pp. 3839-3863, vol. 436.

Polizzi, E., "Density-matrix-based algorithm for solving eigenvalue problems", Physical Review (2009), published Mar. 16, 2009, pp. 115112-1-115112-6, vol. B 79.

Sakurai, T., et al., "A projection method for generalized eigenvalue problems using numerical integration", Journal of Computational and Applied Mathematics (2003), pp. 119-128, vol. 159.

Sakurai, T., et al., "CIRR: a Rayleigh-Ritz type method with contour integral for generalized eigenvalue problems", Hokkaido Mathematical Journal (2007), Revised Jun. 4, 2007, pp. 745-757, vol. 36.

Tang, P.T., et al., "FEAST as a subspace iteration eigensolver accelerated by approximate spectral projection", SIAM Journal on Matrix Analysis and Applications (2014), accepted for publication (in revised form) Jan. 7, 2014, published electronically Apr. 3, 2014, pp. 354-390, vol. 35, No. 2.

Kestyn, J., et al., "FEAST eigensolver for non-Hermitian problems", SIAM Journal on Scientific Computing (2016), accepted for publication (in revised form) Sep. 27, 2016, published electronically Oct. 27, 2016, pp. S772-S799, vol. 38, No. 5.

* cited by examiner

SPECTRAL CLUSTERING OF HIGH-DIMENSIONAL DATA

BACKGROUND

The present application relates generally to computers and computer applications, and more particularly to machine learning, automatically determining a hyper-parameter in machine learning, and clustering high-dimensional data by rational transformation of graph Laplacians, for example, in machine learning.

Machine learning systems such as those employing unsupervised machine learning employ clustering algorithms to group or classify data. In aspects, such clustering may perform computations intensive processing, requiring high computer power resources. In addition, determining hyper-parameters for constructing a machine learning model can be computationally expensive.

BRIEF SUMMARY

The summary of the disclosure is given to aid understanding of a computer system and training in machine learning, for example, for spectral clustering, and not with an intent to limit the disclosure or the invention. It should be understood that various aspects and features of the disclosure may advantageously be used separately in some instances, or in combination with other aspects and features of the disclosure in other instances. Accordingly, variations and modifications may be made to the computer system and/or their method of operation to achieve different effects.

A machine learning system, in an aspect, can include a processor and a memory device coupled with the processor. The system can also include a sensor coupled with the processor. The processor can be configured to receive data from the sensor. The processor can also be configured to create graph Laplacian of the data and store the graph Laplacian in the memory device. The processor can also be configured to compute spectral characteristic by applying density of states and detect spectral gaps in an unsupervised manner in the spectral characteristic to determine r number of clusters, where r is a hyper-parameter for machine learning. The processor can also be configured to compute a range space of a rational matrix of the graph Laplacian. The processor can also be configured to train an unsupervised machine learning model based on the hyper-parameter r to cluster the received data, wherein to train the unsupervised machine learning model, the processor is configured to perform K-means clustering on the range space of rational matrix of the graph Laplacian using r as the number of clusters, the K-means clustering trained to return r clusters of the received data.

A computer-implemented machine learning method, in an aspect, can include receiving data from the sensor. The method can also include creating graph Laplacian of the data and storing the graph Laplacian in the memory device. The method can also include computing spectral characteristic by applying density of states and detecting spectral gaps in an unsupervised manner in the spectral characteristic to determine r number of clusters, r being a hyper-parameter for machine learning. The method can also include computing a range space of a rational matrix of the graph Laplacian. The method can also include training an unsupervised machine learning model based on the hyper-parameter r to cluster the received data, wherein to train the unsupervised machine learning model, the processor is configured to perform K-means clustering on the range space of rational matrix of the graph Laplacian using r as the number of clusters, the K-means clustering trained to return r clusters of the received data.

A computer readable storage medium storing a program of instructions executable by a machine to perform one or more methods described herein also may be provided.

Further features as well as the structure and operation of various embodiments are described in detail below with reference to the accompanying drawings. In the drawings, like reference numbers indicate identical or functionally similar elements.

DETAILED DESCRIPTION

Figure 1:
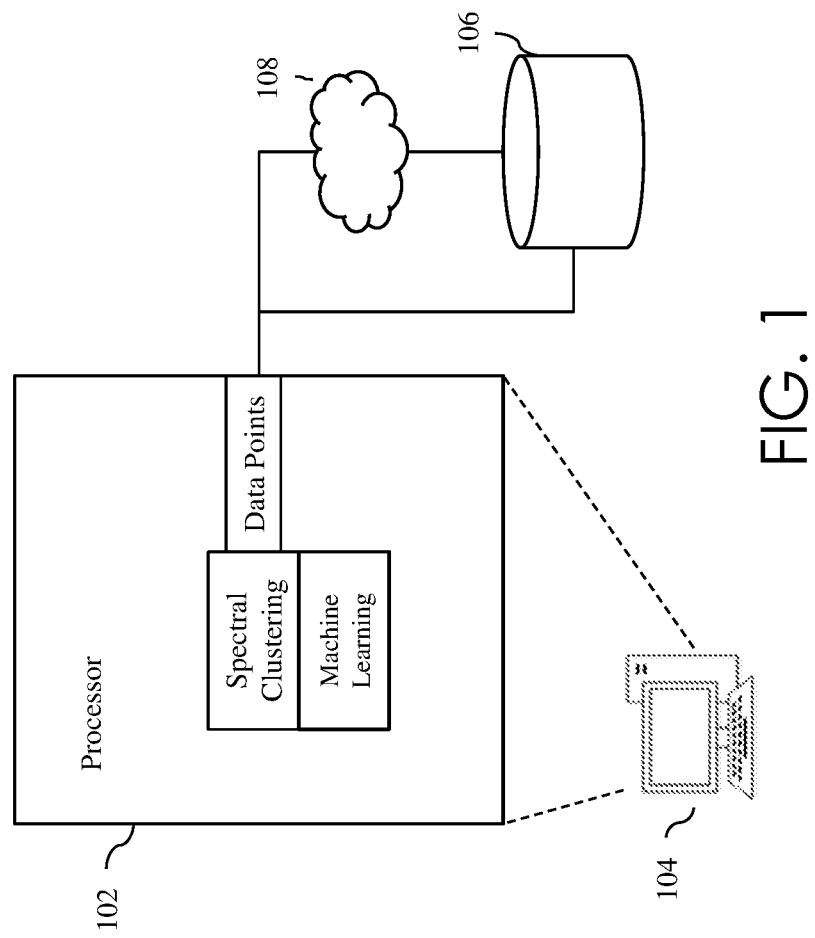
FIG. 1 is a diagram illustrating components of a system in an embodiment for spectral clustering.

A system and method can be provided for spectral clustering, for instance, clustering high-dimensional data by rational transformation of graph Laplacians. Some machine learning techniques and applications use clustering or clustering algorithms to classify or make predictions on given data. For example, in marketing domain, maximizing potential profit can include determining correct groups of targets, the groups, for example, determined based on clustering. Clustering aims to group together given data representing some real world entities (e.g., objects, events, people) with similar characteristics and similar tendencies. For instance, a group of customers with similar characteristics and tendencies can be provided a focused marketing copy directed to the interests of that group. As another example, in a case where the allocation of medical resources can run at a critical low, clustering patients in distinct groups according to their similarity can result in efficient use of resources since each cluster can be treated separately. Further, it may be that patients from the same group can require similar treatment, and such grouping may aid in providing treatments to patients more efficiently.

Other applications can include, but are not limited to, e.g.: in artificial intelligence area—graph analysis, analysis of stability and robustness of deep neural networks (DNNs) and recurrent neural network (RNNs), recommender systems, computational geometry; in quantum area—computational chemistry, quantum topological data analysis (TDA), time-dependent density functional theory (TDDFT); in Internet of Things (IoT) area—in automotive, transient stability analysis of Navier-Stokes Solver, diffusion model study for crystal growth simulation, modal analysis of dissipative magnetohydrodynamics (MHD), vibration analysis.

A system and method in an embodiment can accelerate runtime of training machine learning models in such applications, such as unsupervised machine learning where clustering is performed, by speeding up hyper-parameter computations such as eigenvalue computations. The system and method in an embodiment features rational transformations and, at the same time, can avoid the need to estimate the number of eigenvalues located inside a disk.

Spectral clustering can be used in unsupervised learning technique. In spectral clustering, a goal can be, given n data points organized as rows of a matrix Y, to group the data points into a set of different clusters. Let G denote the similarity graph of the data collection Y of n data points. Moreover, let the n×n matrix W denote the weights between the nodes of G. The graph Laplacian matrix is then equal to A=D−W, where D is n×n matrix diagonal matrix whose i-th diagonal entry is equal to the sum of weights of the i-th node of G. One may compute an orthonormal basis Z of the invariant subspace span $(x^{(1)}, \ldots, x^{(r)})$, where $1 <= r <= n$ and $x^{(1)}$ denotes the eigenvector associated with the i-th algebraically smallest eigenvalue of A. The final clustering of the data collection is determined by applying k-means to cluster the n data points determined by the rows of the n×r matrix Z. Matrix Z can be seen as a spectral embedding of Y onto the r-dimensional subspace. "r" can be considered a hyper-parameter in machine learning.

Challenges with spectral clustering can include determining how to set r. Computing span $(x^{(1)}, \ldots, x^{(r)})$ can be very challenging and computationally expensive. The system and method in an embodiment sets r automatically by detecting spectral gaps in an unsupervised manner. The system and method in an embodiment sets Z equal to the basis of range $(\rho(A)) \supseteq span (x^{(1)}, \ldots, x^{(r)})$ where $\rho$ is a rational matrix function. The system and method in an aspect leads to faster computation, requiring less computing resources and more practical spectral clustering.

FIG. 1 is a diagram illustrating components of a system in an embodiment for spectral clustering. The components shown include computer-implemented components, for instance, implemented and/or run on one or more hardware processors, or coupled with one or more hardware processors. One or more hardware processors, for example, may include components such as programmable logic devices, microcontrollers, memory devices, and/or other hardware components, which may be configured to perform respective tasks described in the present disclosure. Coupled memory devices may be configured to selectively store instructions executable by one or more hardware processors.

A processor may be a central processing unit (CPU), a graphics processing unit (GPU), a field programmable gate array (FPGA), an application specific integrated circuit (ASIC), another suitable processing component or device, or one or more combinations thereof. The processor may be coupled with a memory device. The memory device may include random access memory (RAM), read-only memory (ROM) or another memory device, and may store data and/or processor instructions for implementing various functionalities associated with the methods and/or systems described herein. The processor may execute computer instructions stored in the memory or received from another computer device or medium.

A processor 102 may perform machine learning, for example, a machine learning model performing a prediction and/or classification. An example machine learning model may perform unsupervised machine learning classification on a dataset or data points. In an embodiment, the machine learning model may perform spectral clustering for performing a classification or prediction. The dataset or data points can be stored on a storage device 106, e.g., stored locally or remotely, and/or received from a network 108. To perform spectral clustering, the processor 102 may form a graph Laplacian matrix A. For instance, the processor may take dataset or data points representative of data for classification (e.g., email data for filtering, computer traffic data for security, and/or others) and create a graph Laplacian matrix. The processor may determine an eigeninterval [0, β] containing the r smallest eigenvalues of A. For example, the processor may compute a spectral characteristic by applying density of states. The processor may capture an orthonormal basis Z of range $(\rho(A))$, where $\rho(X) \approx 0$ for any $X \notin [0, \beta]$. The processor may apply a k-means algorithm to Z and return the r clusters. $\rho(A)$ is a matrix function produced by rational approximation of the step function in $[0, \beta]$.

Figure 2:
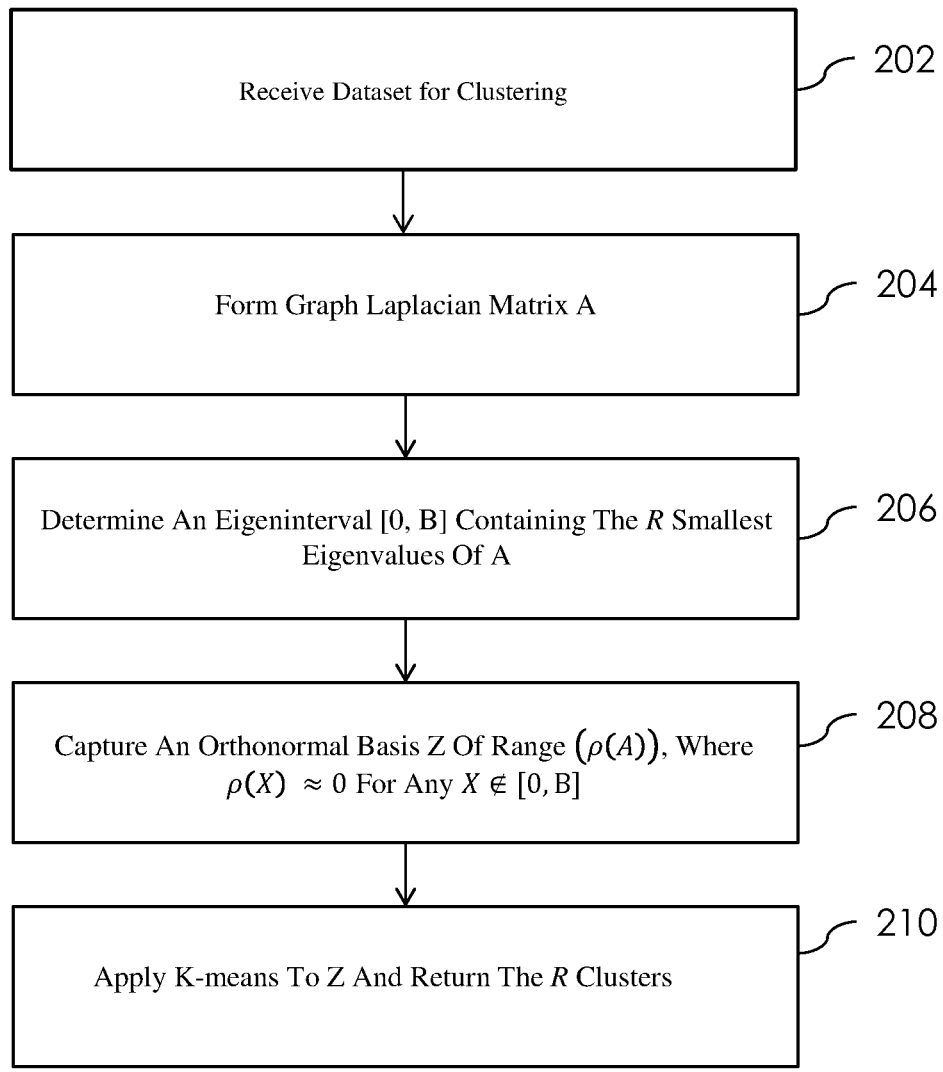
FIG. 2 is a flow diagram illustrating a method in an embodiment for spectral clustering. The method can be performed by one or more computer processors.

FIG. 2 is a flow diagram illustrating a method in an embodiment for spectral clustering. The method can be performed by one or more computer processors. At 202, input data can be received, which is to be clustered. The input data may be in a structured form. In an embodiment unstructured data can be received and structured into a format appropriate for machine learning processing.

At 204, the method includes, given data points (the input data), forming a graph Laplacian matrix A. For instance, an adjacency matrix of the data points representing connections (or weighted connections) between two or more of the data points can be generated from the given data points. A diagonal matrix can also be generated. The diagonal matrix has in the diagonal the number of the connections a data point has in the adjacency matrix. Other entries in the diagonal matrix are set to zeros. For example, let G denote the similarity graph of the data collection Y of n data points. Let the n×n matrix W denote the weights between the nodes of G. The graph Laplacian matrix is generated as A=D−W, where D is n×n matrix diagonal matrix whose i-th diagonal entry is equal to the sum of weights of the i-th node of G.

At 206, the method includes determining an eigeninterval [0, β] containing the r smallest eigenvalues of A. For example, the following illustrates automatically detecting the number of clusters in an embodiment, e.g., a hyper-parameter for K-means clustering. Suppose G has r connected components. A is block-diagonal and has r zero eigenvalues. The presence of r (approximately) disconnected groups of data results to a cluster of the algebraically smallest r eigenvalues close to zero. The system and method in an embodiment determine a real interval [0, β] which (approximately) includes only the r algebraically smallest eigenvalues of A.

Figures 3A, 3B:
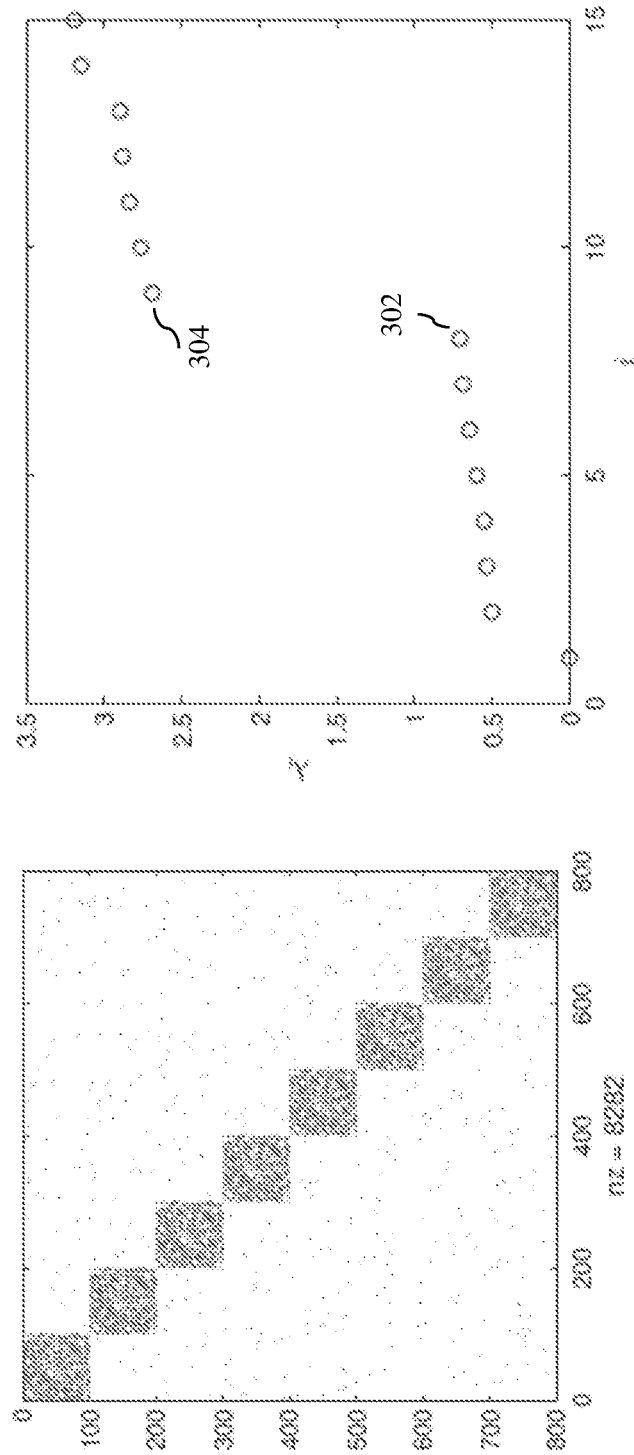
FIGS. 3A and 3B show an example of graph Laplacian A formed by a dataset in which there exist eight clusters which are loosely connected with each other in an embodiment.

FIGS. 3A and 3B show an example of graph Laplacian A formed by a dataset in which there exist eight clusters which are loosely connected with each other in an embodiment. In FIG. 3B shows the gap between eigenvalues λ8 302 and λ9 304.

Figure 4B:
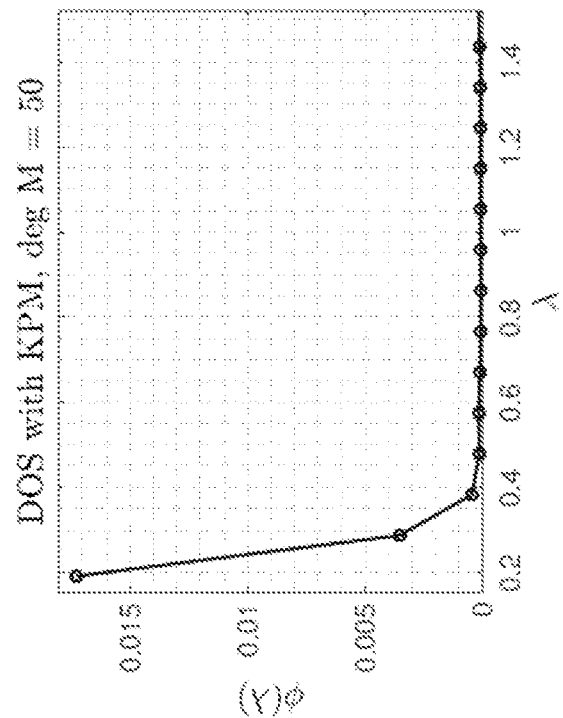
FIGS. 4A and 4B show an example density of states (DOS) plot in an embodiment.
Figure 4A:
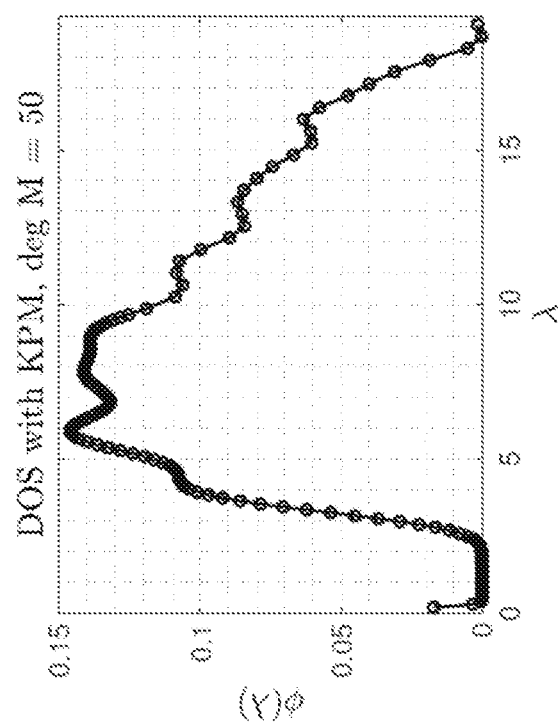

Let ϕ(t) denote the probability of finding eigenvalues of A in a given infinitesimal interval near t (i.e., density of states). A high value of ϕ(t) is expected around the origin (0, 0 coordinate), followed by a plateau where ϕ(t) is close to zero. FIGS. 4A and 4B show an example density of states (DOS) plot in an embodiment. A processor may start scanning from the left, and set β equal to the value of t where ϕ(t) becomes (approximately) zero. A threshold value can be set for determining whether a value is to be considered a "zero". Using Density of states (DOS) obtained by Kernel Polynomial Method, the processor may determine to set β=0.5. For example, a processor may compute a spectral characteristic by applying density of states.

Referring to FIG. 2, at 208, the method includes capturing an orthonormal basis Z of range (ρ(A)), where ρ(X)≈0 for any X∉[0, β]. For instance, a filtering function can be applied to find a range space, also referred to as a low dimensional subspace or embedding. For instance, latent embedding can uncover hidden interconnections in the data points. The method, for example, can automatically detect embedding of subspace in spectral clustering.

The following illustrates computing the embedding subspace in an embodiment. For example, a filtering function can be used to determined range space, e.g., low dimensional subspace. The processor aims to compute span (Z)=range $(x^{(1)}, \ldots, x^{(r)})$. This is equivalent to computing range $(\Sigma_{i=1}^{n} \rho(\lambda_i)x^{(i)}(\hat{x}^{(i)})^H)$ where ρ(x)=1, x∈[0, β], and zero elsewhere. $x^{(1)}, \ldots, x^{(r)}$ represent low dimensional space (e.g., subspace embedding). The processor in an embodiment uses $$\rho(\zeta) = \sum_{j=1}^{N} \frac{\omega_j}{\zeta - \zeta_j}$$

where the complex pairs $\{\omega_j, \zeta_j\}_{j=1, \ldots, N}$ denote the weights and nodes of the N-trapezoidal rule, respectively. It follows that $\rho(A)=\Sigma_{j=1}^{N} \omega_j(A-\zeta_j I)^{-1}$. The superscript "−1" denotes the inverse of a matrix. $\zeta_j$ is a complex number derived by the N-point midpoint rule approximation of the step function in [0, β]. Herein, N can be any positive integer. N can be given or pre-defined. The last step in this computing is to compute the range of ρ(A). Computing the range of ρ(A) includes finding all linear combinations of column vectors of ρ(A).

Figure 5B:
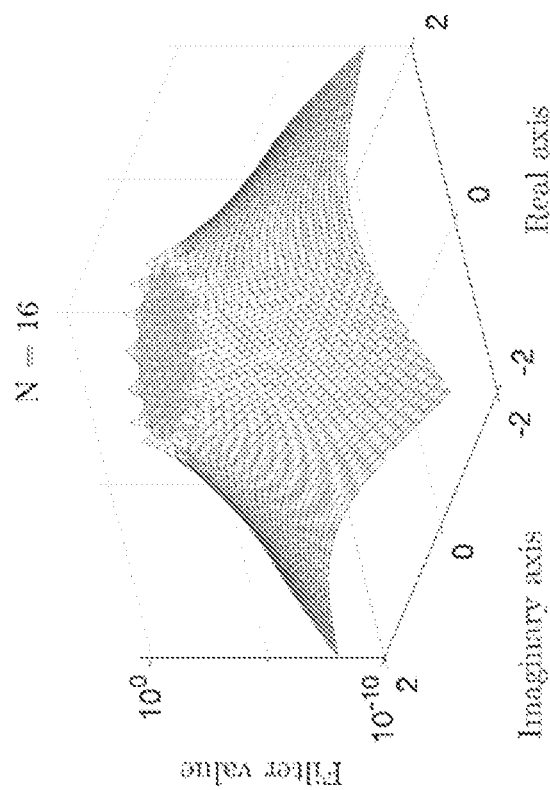
FIGS. 5A and 5B show graphical illustrations of the approximation of the unit circle by $\rho(\zeta)$ in an embodiment.
Figure 5A:
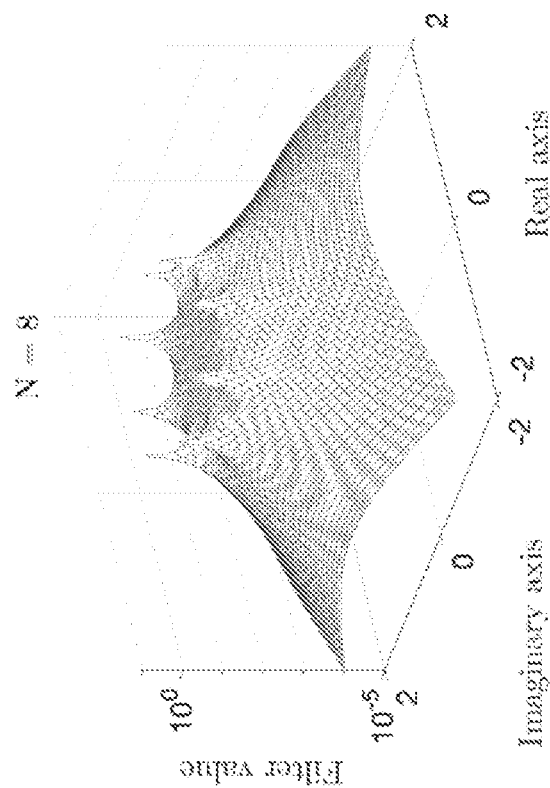

FIGS. 5A and 5B show graphical illustrations of the approximation of the unit circle by ρ(ζ) in an embodiment. The figures plot the magnitude of a rational filter ρ(ζ) defined on the unit disk ($\mathcal{D} \equiv \{|z|:|z|\leq 1\}$) with the trapezoidal rule of order N=8 (FIG. 5A) and N=16 (FIG. 5B). In particular, the approximation of P(ζ) by ρ(ζ) at the center of the disk $\mathcal{D}$ converges exponentially with respect to N.

Referring to FIG. 2, at 210, the method includes applying K-means algorithm to Z and returning the r clusters. K-means algorithm is a clustering technique, which given a number r, returns r clusters from the data points (cluster the data points into r clusters). In this way, an unsupervised machine learning model can be trained to cluster the received dataset into r clusters.

Figure 6:
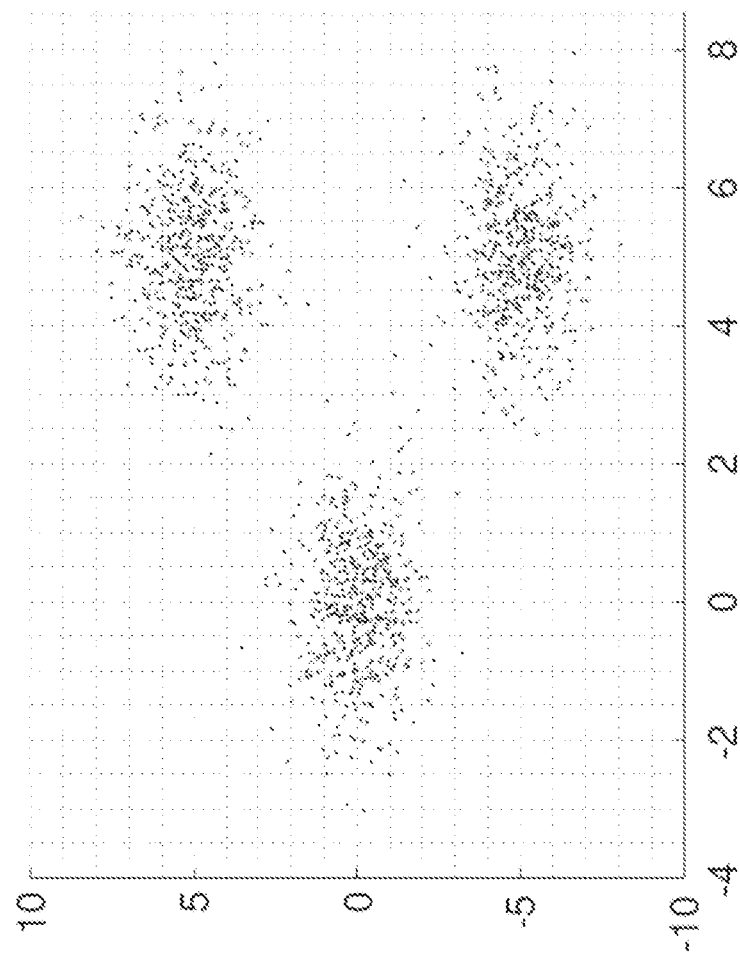
FIG. 6 shows an example data set in an embodiment.
Figure 7A:
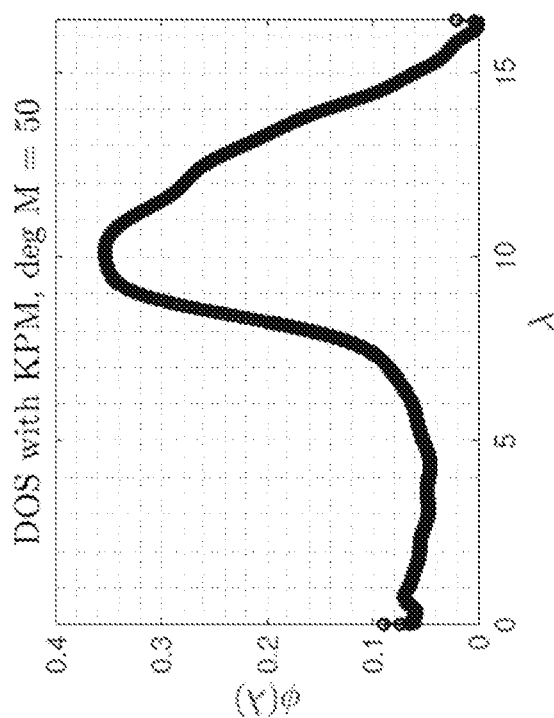
FIGS. 7A and 7B show an example DOS characteristics in an embodiment.
Figure 7B:
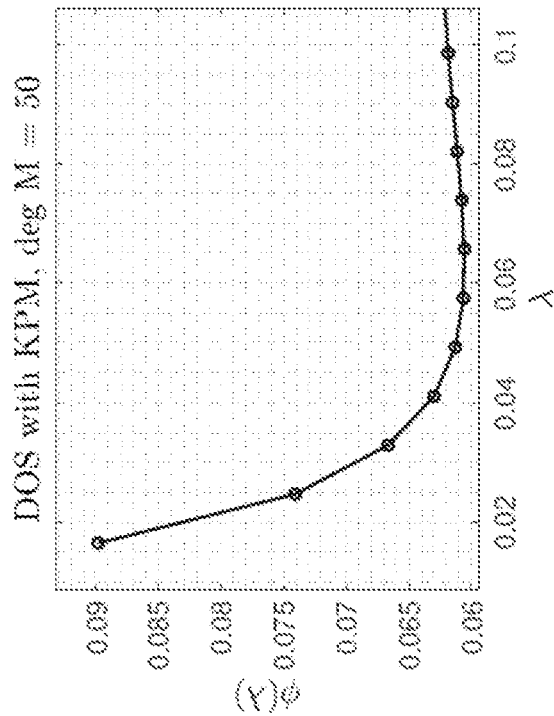
Figure 8:
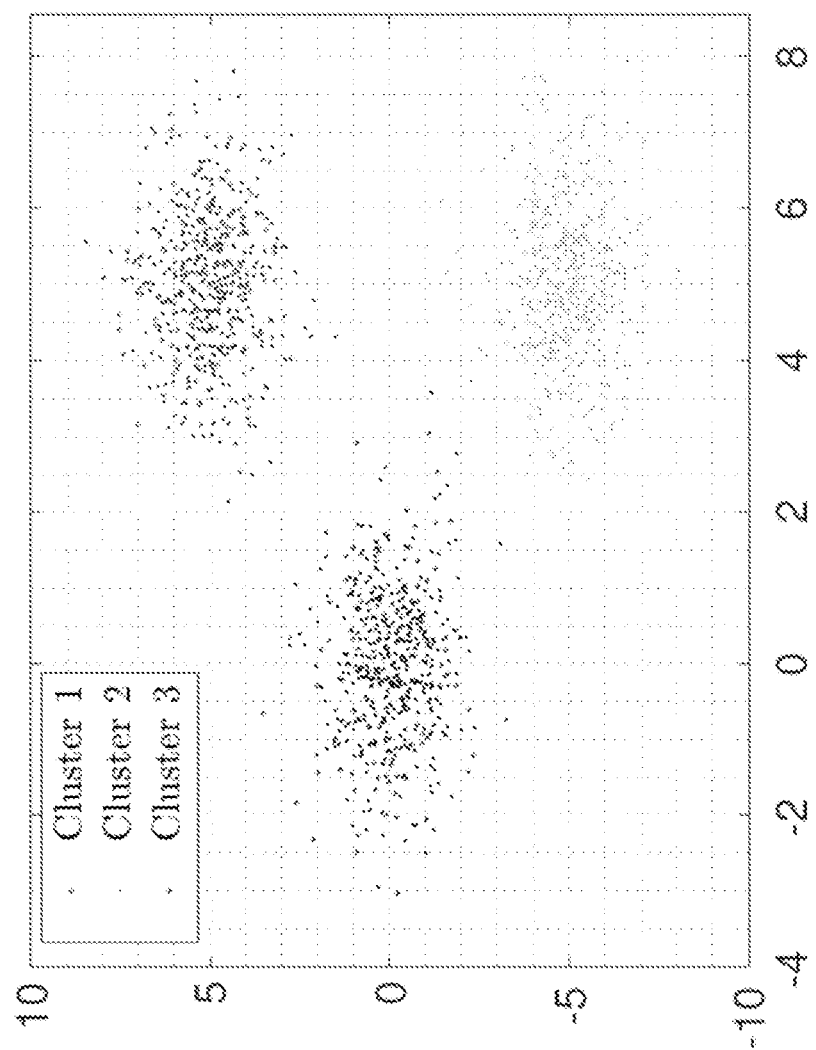
FIG. 8 shows clustered results in an embodiment.

FIG. 6 shows an example data set in an embodiment. A set of 500 points is clustered on the two-dimensional space. The processor may form the associated graph Laplacian and plot the density of state (DOS) characteristic. FIGS. 7A and 7B show an example DOS characteristic in an embodiment. By examining the spectral characteristic, the processor determines that β=0.06. The eigenvalues of A are 1.5e-16, 5.2e-15, 0.0079, 0.0940, . . . and so on. The processor notices the gap between $\lambda_3$ and $\lambda_4$, and therefore, there exists three clusters. The processor sets N=16 and computes a basis of the range of ρ(A). The processor applies or runs K-means algorithm and can cause to present a plot of the results. FIG. 8 shows an example plot of clustering results in an embodiment. For example, the plot shows three clusters determined by the method.

In an embodiment, a computer system may perform computation of all eigenvalues located inside a disk without estimation of their number. A system can compute eigenvalues of non-Hermitian matrices located inside a disk in the complex plane. The system can also return the corresponding eigenvectors at a minimal additional cost.

In an embodiment, a system can be based on rational filtering to compute a few eigenvalues of non-Hermitian matrix pencils located inside a certain disk in the complex domain. In an embodiment, the system approximates the sought eigenvalues and associated eigenvectors by harmonic Rayleigh-Ritz projections in which the ansatz subspace is built by computing range spaces of matrix functions. These matrix functions are based on rational functions and are constructed such that directions associated with non-sought eigenvalues are dampened to (approximately) zero. These rational matrix functions are also combined with matrix partitionings to reduce the overall complexity of the system.

A drawback of current approaches is that they require the number of eigenvalues located inside a disk (or an estimation of it) to be given as input. Compared with existing eigenvalue solvers based on rational matrix functions, the system finds an eigenvalue solver without requiring estimation of the number of eigenvalues located inside the disk, and uses less computational effort. It is to be noted that an inaccurate estimation can lead to severe performance degradation or failure to capture all required eigen pairs. In an embodiment, the system bypasses this issue by dynamically increasing the dimension of the projection subspace and relies on a carefully designed mechanism to halt the iteration once all sought eigen pairs are captured.

Rational filtering eigenvalue solvers are often combined with (harmonic) Rayleigh-Ritz procedures in which the ansatz projection subspace is built by exploiting a (complex) rational transformation of the input matrix pencil. These transformations are constructed in a way such that eigenvalues inside a given disk are amplified while the unwanted ones (those outside the disk) are dampened to (approximately) zero. Applying a projection scheme to the transformed matrix pencil can then enhance the convergence towards the sought invariant subspace.

In an embodiment, the system may first apply a rational transformation to the provided matrix pencil. A disk is also given as input, and the desire is to compute all eigenvalues (and associated eigenvectors) located inside this disk. The system may apply a rational transformation that removes the part of the problem associated with eigenvalues located outside the disk. The system may then proceed to capture the range space of the filtered matrix pencil. An oblique projection can be performed to capture the sought eigenvalues.

Consider the following eigenvalue problem, Ax=λMx, where matrices A and M are sparse and the pencil (A, M) is regular and diagonalizable. The pencil (A, M) has n eigenpairs which can be denoted by $(\lambda_i, x^{(i)})$, i=1, . . . , n. Consider that one is interested in computing the $n_{ev}$ eigenpairs ($\lambda i$, $x^{(i)}$), for which $\lambda_i \in \mathcal{D}$. When A and M are Hermitian, $\mathcal{D}$ is an interval on the real plane.

The following illustrates Harmonic Rayleigh-Ritz (HRR) projection in an embodiment. Let matrix Z represent a basis of some subspace $\mathcal{Z}$ from which we extract approximations of the sought eigenvectors of the matrix pencil (A, M). The HRR procedure extracts approximate eigenpairs of the matrix pencil (A, M) which are of a scalar-vector form ($\tilde{\lambda}$, Zq). The pair ($\tilde{\lambda}$, q) is obtained by solving the eigenvalue problem $$Z^H(A-\zeta M)^H(A-\zeta M)Zq=(\tilde{\lambda}-\zeta)Z^H(A-\zeta M)^H MZq,$$

where $\zeta \in \mathbb{C}$ is the center of $\mathcal{D}$.

The main task then becomes the computation of a subspace $\mathcal{Z}$ which includes an approximate invariant subspace associated with $n_{ev}$ sought eigenvalues $\lambda_1, \ldots, \lambda_{n_{ev}}$. These eigenvalues and associated eigenvectors are then approximated by a subset of the Ritz pairs. A proposed system may consider ansatz subspaces of the form $\mathcal{Z} = \text{range}(\rho(M^{-1}A))$ for some function $\rho$.

The following illustrates a matrix system transformation in an embodiment.

Let $\rho: \mathbb{C} \to \mathbb{C}$, be a scalar function that is defined over $\Lambda(A, M)$. Since (A, M) is diagonalizable, applying $\rho$ to matrix $M^{-1}A$ is equivalent to:

$$\rho(M^{-1}A)=\Sigma_{i=1}^n \rho(\lambda_i)x^{(i)}(\hat{x}^{(i)})^H M.$$

Assume $\rho(\lambda i) \neq 0$, $i=1, \ldots, n_{ev}$.

It follows that span ($x^{(1)}, \ldots, x^{(n_{ev})}$)$\subseteq$range ($\rho(M^{-1} A)$) and thus setting $\mathcal{Z} = \text{range}(\rho(M^{-1} A))$ will also capture the invariant subspace associated with the eigenvalues $\lambda_1, \ldots, \lambda_{n_{ev}}$, located inside the disk $\mathcal{D}$.

The following illustrates a pseudo procedure for capture of range in an embodiment.
Procedure
System Prototype
0. Inputs: $\rho: \mathbb{C} \to \mathbb{R}$, $\mathcal{D}$, Z=0
1a. For k=1, ..., n
2. Set r to a random n×1 vector
3. Z=[Z, $\rho(M^{-1} A)r$]
4. If the range of matrix is captured $\rho(M^{-1} A)$, break
1b. End
  Solve the eigenvalue problem in Harmonic Rayleigh-Ritz (HRR) projection above and return all Ritz values $\theta \in \mathcal{D}$ and associated Ritz vectors The following illustrates an example of ideal transformation in an embodiment. An ideal function $\rho$ can be defined by the contour integral $$\mathcal{P}(\zeta) := \frac{-1}{2\pi i}\int_r \frac{1}{\zeta - v}dv,$$

where the complex contour $\Gamma$ denotes the circumference of the disk $\mathcal{D}$, and the integration is performed counter-clockwise. By Cauchy's residue theorem it follows that $\mathcal{P}(\zeta)=1$ for any $\zeta \in \mathcal{D}$, and zero otherwise. Applying the above to (A, M) yields $$\mathcal{P}(M^{-1}A) := \frac{-1}{2\pi i}\int_r (M^{-1}A - vI)^{-1} dv = \sum_{k=1}^{n_{ev}} x^{(i)}(\hat{x}^{(i)})^H M.$$

The method of capturing the range in an embodiment may terminate after exactly $n_{ev}$ iterations.

The following illustrates an example of numerical approximation of the ideal transformation in an embodiment. In practice, $\rho(\zeta)$ will be approximated by numerical quadrature which leads to a rational (filter) function of the form $$\rho(\zeta) = \sum_{j=1}^n \frac{\omega_j}{\zeta - \zeta_j},$$

where the integer N denotes the order of the approximation, and the complex pairs $\{\omega_j, \zeta_j\}_{j=1,\ldots,N}$ denote the weights and nodes of the quadrature rule, respectively. Then there can be $$\rho(M^{-1}A)=\Sigma_{j=1}^N \omega_j(M^{-1}A-\zeta_j I)^{-1}=\Sigma_{j=1}^N \omega_j(A-\zeta_j M)^{-1}M.$$

The system and method in an embodiment can accelerate machine learning algorithm by speeding up the underlying eigenvalue computations. A system in an embodiment disclosed herein can be more practical since it does not require an estimation of the number of eigenvalues located inside a disk.

Figure 9:
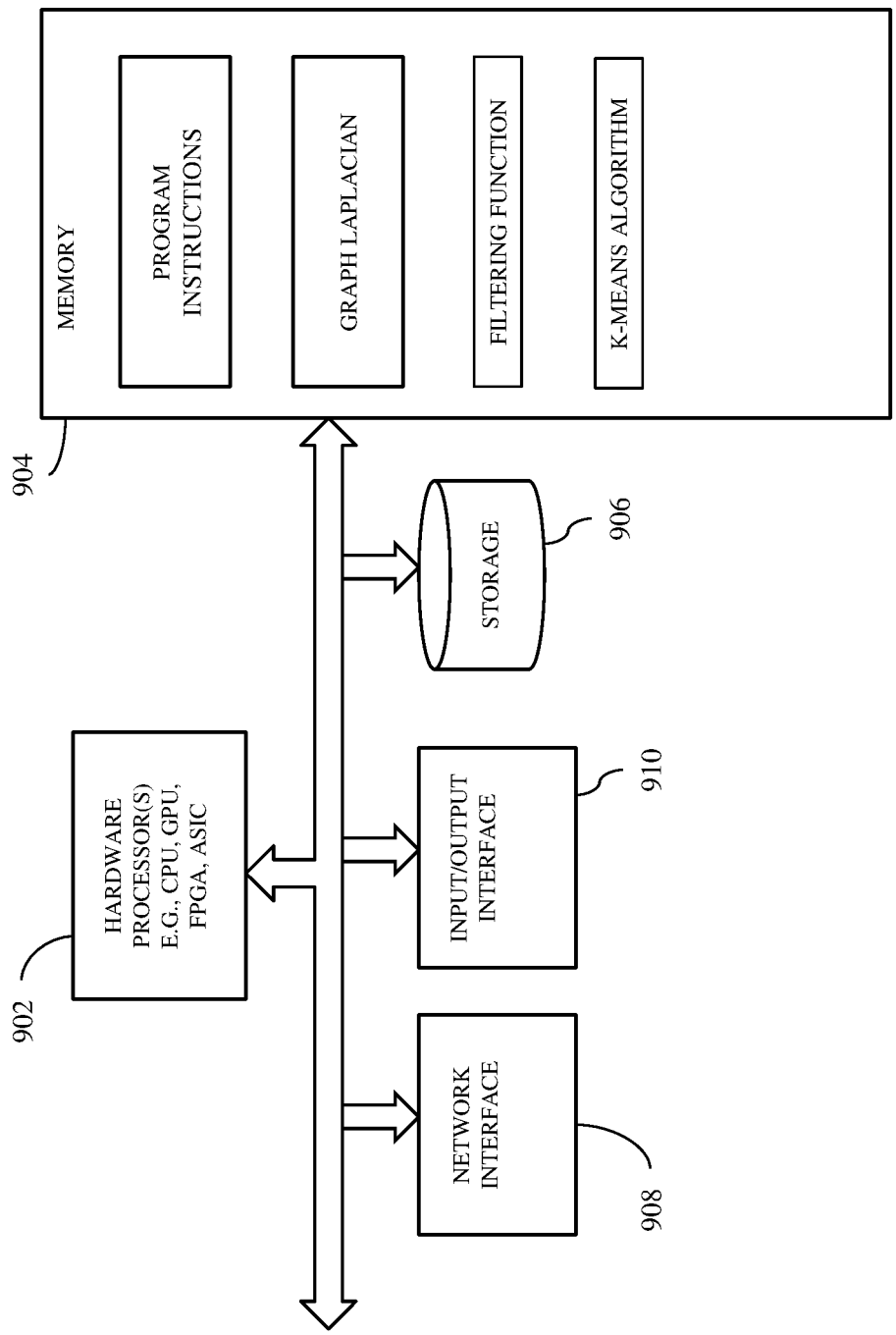
FIG. 9 is a diagram showing components of a system in one embodiment that can perform machine learning, for example, an unsupervised machine learning, which can include spectral clustering of input data.

FIG. 9 is a diagram showing components of a system in one embodiment that can perform machine learning techniques, for example, an unsupervised machine learning, which can include spectral clustering of input data. One or more hardware processors 902 such as a central processing unit (CPU), a graphic process unit (GPU), and/or a Field Programmable Gate Array (FPGA), an application specific integrated circuit (ASIC), and/or another processor, may be coupled with a memory device 904, and generate a prediction model and recommend communication opportunities. A memory device 904 may include random access memory (RAM), read-only memory (ROM) or another memory device, and may store data and/or processor instructions for implementing various functionalities associated with the methods and/or systems described herein. One or more processors 902 may execute computer instructions stored in memory 904 or received from another computer device or medium. A memory device 904 may, for example, store instructions and/or data for functioning of one or more hardware processors 902, and may include an operating system and other program of instructions and/or data. One or more hardware processors 902 may receive input include data points for clustering, which can include entities and/or attributes about entities. At least one hardware processor 902 can perform spectral clustering on the received input data, for example, described here with reference to the figures. Input data may be stored in a storage device 906 or received via a network interface 908 from a remote device, and may be temporarily loaded into a memory device 904 for performing machine learning, e.g., spectral clustering. A machine learning model performing such spectral clustering may be stored on a memory device 904, for example, for running by one or more hardware processors 902. One or more hardware processors 902 may be coupled with interface devices such as a network interface 908 for communicating with remote systems, for example, via a network, and an input/output interface 910 for communicating with input and/or output devices such as a keyboard, mouse, display, and/or others.

Figure 10:
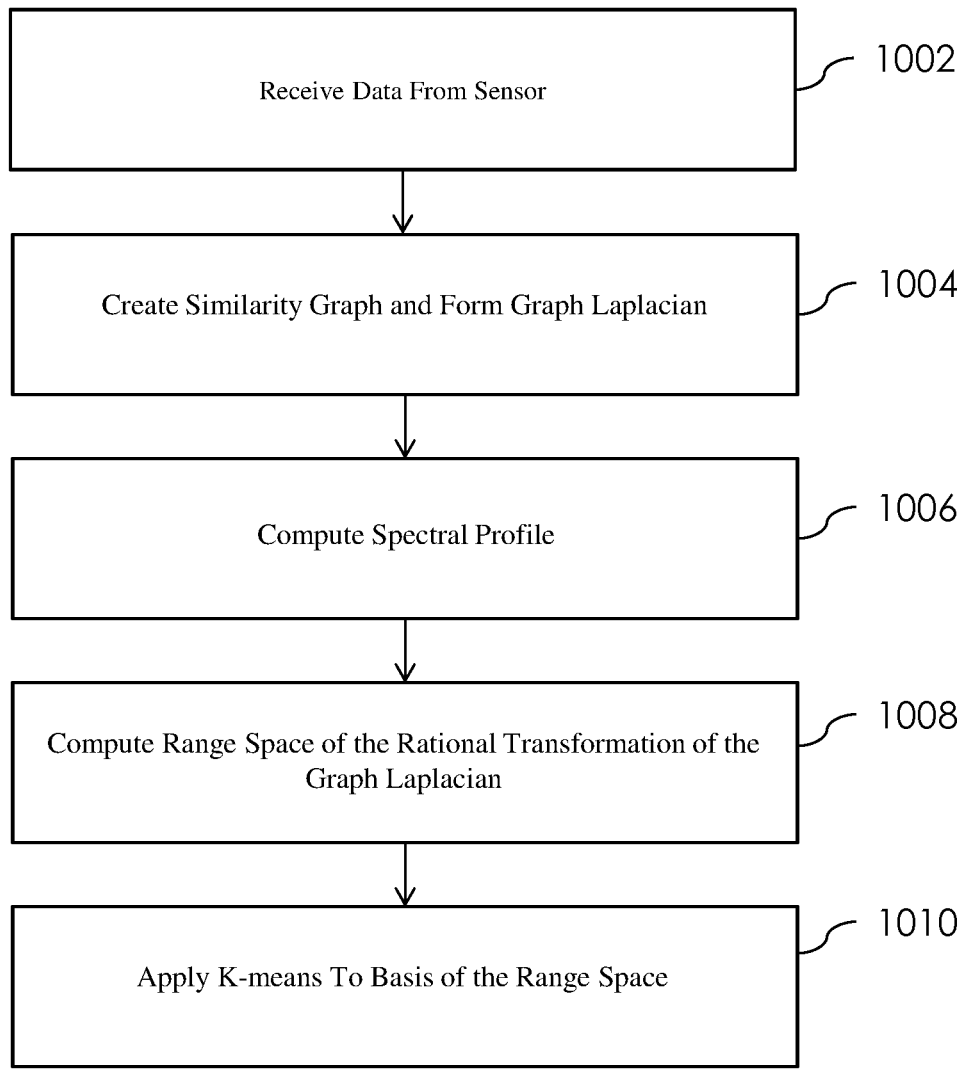
FIG. 10 is a flow diagram illustrating machine learning performing spectral clustering of patients according to their similarity attributes in an embodiment.

FIG. 10 is a flow diagram illustrating machine learning performing spectral clustering of patients according to their similarity attributes in an embodiment. At 1002, data from healthcare diagnosis apparatus or sensor can be received.

One or more processors can be communicatively connected to one or more healthcare diagnosis apparatus or sensor and can automatically receive such data without manual interaction. The permission from patients to transmit or receive such information between automated processing components can be preset or pre-established. Examples of specific data can include multiple vital sign data of each patient, which may be highly correlated. The machine learning using spectral clustering described herein may allow for individual and unsupervised pattern discovery, identifying patient subgroups based on similarity of the patients' characteristics.

At 1004, based on the received data, a processor may create a similarity graph and compute its graph Laplacian, for example, as described above.

At 1006, a processor may compute a spectral characteristic by applying density of states and detect spectral gaps in an unsupervised manner in the spectral characteristic to determine r, representing number of clusters. "r" is a hyperparameter used in unsupervised machine learning such as K-means algorithm. The density of states provides a signal f(t) which denotes the probability of finding an eigenvalue of matrix A in a given infinitesimal interval around t.

At 1008, a processor may compute the range space of the rational transformation of the graph Laplacian. Briefly, the range space is also referred to as the column space, and includes the set of all linear combinations of the column vectors of the rational transformation of the graph Laplacian. Techniques in linear algebra can compute such range space. A filtering algorithm may be used to compute the range space. In an aspect, standard know technique or techniques can be used to compute the range space.

At 1010, a processor may train an unsupervised machine learning model based on or using the determined hyperparameter r. The unsupervised machine learning model can be a K-means machine learning model. For example, a processor may apply a K-means clustering algorithm to the basis of the range space computed at 1008 using r. For example, the basis of the range space computed at 1008 can be determined, e.g., using techniques in linear algebra, and the K-means clustering algorithm can be applied to the computed basis of the range space. The K-means clustering algorithm returns clusters of the received input data, i.e., the input data clustered into r clusters.

In an embodiment, different types of patient data can be received and a patient similarity network or graph can be built. Based on spectral clustering described herein, patients can be clustered into groups such as high-risk or low-risk for a type of disease.

In another embodiment, the method described with respect to FIG. 10 can be used in detecting network data traffic, for example, computer data traffic, for example, to filter data for security purposes. In such an embodiment, the sensor can include computer network data monitors or devices. An unsupervised machine learning model (e.g., spectral clustering using K-means) can be trained to classify the computer network traffic data into r clusters of different security levels, for example, for protection of computer system from computer viruses, malware, ransomware or the like. In an embodiment, the method can also include running or using the trained unsupervised machine learning model to control the computer system and data traffic to protect the computer system from such computer viruses, malware, ransomware or the like. For instance, using the trained unsupervised machine learning model can detect, for example, cluster an incoming data traffic in real-time, and prevent such data from entering the computer system. For instance, the model takes the incoming real-time traffic data and returns the cluster that the incoming real-time traffic data belongs to, according to the training of that the model.

Yet in another embodiment, the method described with respect to FIG. 10 can be used in clustering or classifying any other types of data.

Figure 11:
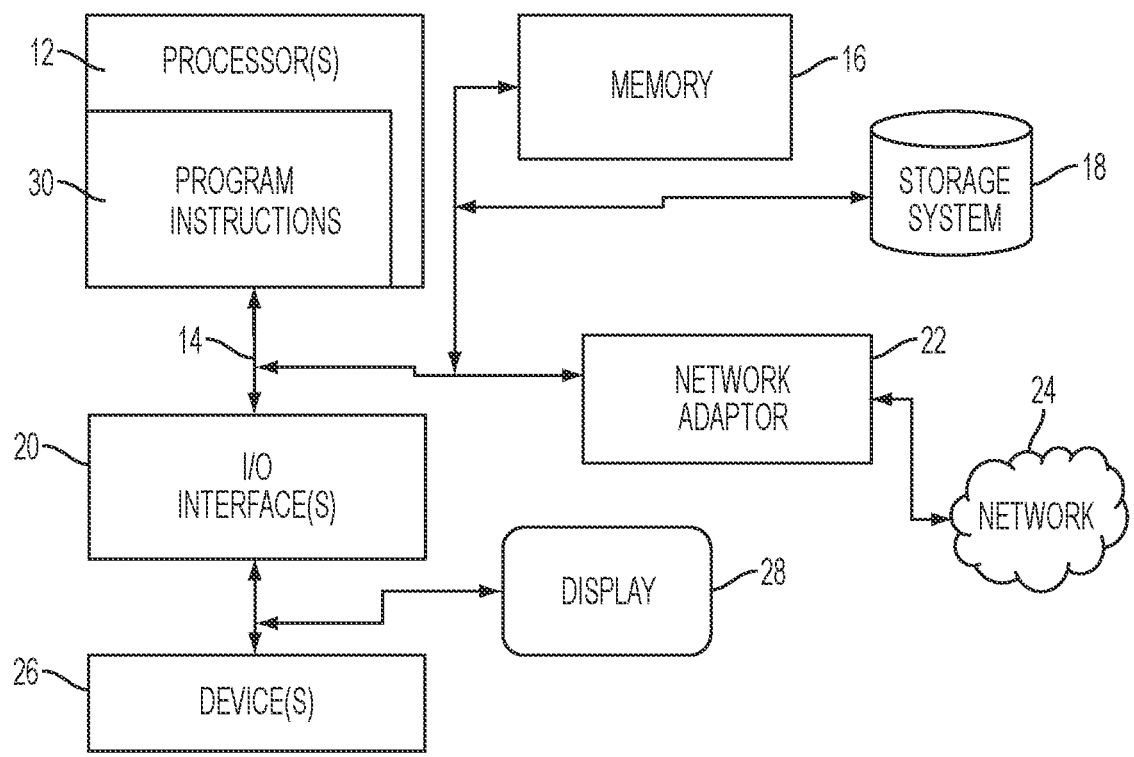
FIG. 11 illustrates a schematic of an example computer or processing system that may implement a system according to one embodiment.

FIG. 11 illustrates a schematic of an example computer or processing system that may implement a system in one embodiment. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 11 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being run by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a module 30 that performs the methods described herein. The module 30 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

It is understood in advance that although this disclosure may include a description on cloud computing, implementation of the teachings recited herein are not limited to a cloud computing environment. Rather, embodiments of the present invention are capable of being implemented in conjunction with any other type of computing environment now known or later developed. Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 12:
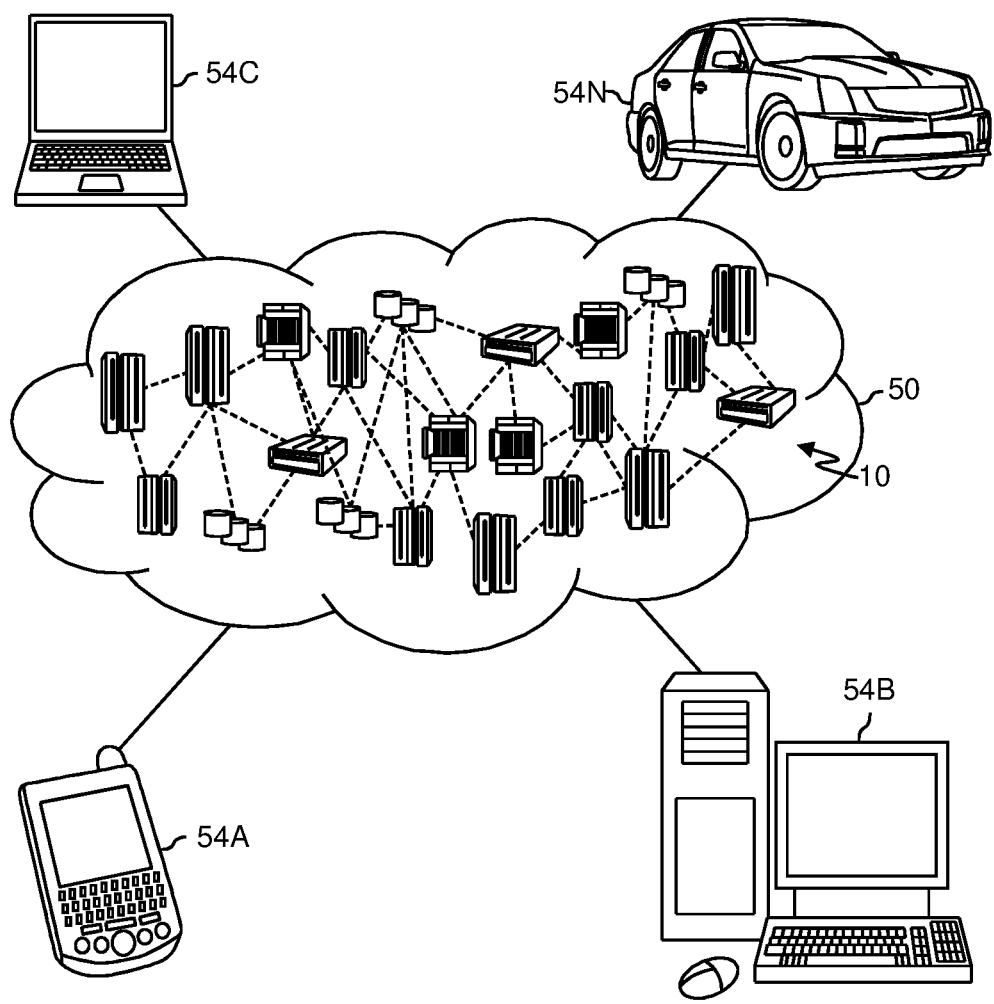
FIG. 12 illustrates a cloud computing environment in one embodiment.

Referring now to FIG. 12, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 12 are intended to be illustrative only and that computing nodes 10 and cloud computing environment 50 can communicate with any type of computerized device over any type of network and/or network addressable connection (e.g., using a web browser).

Figure 13:
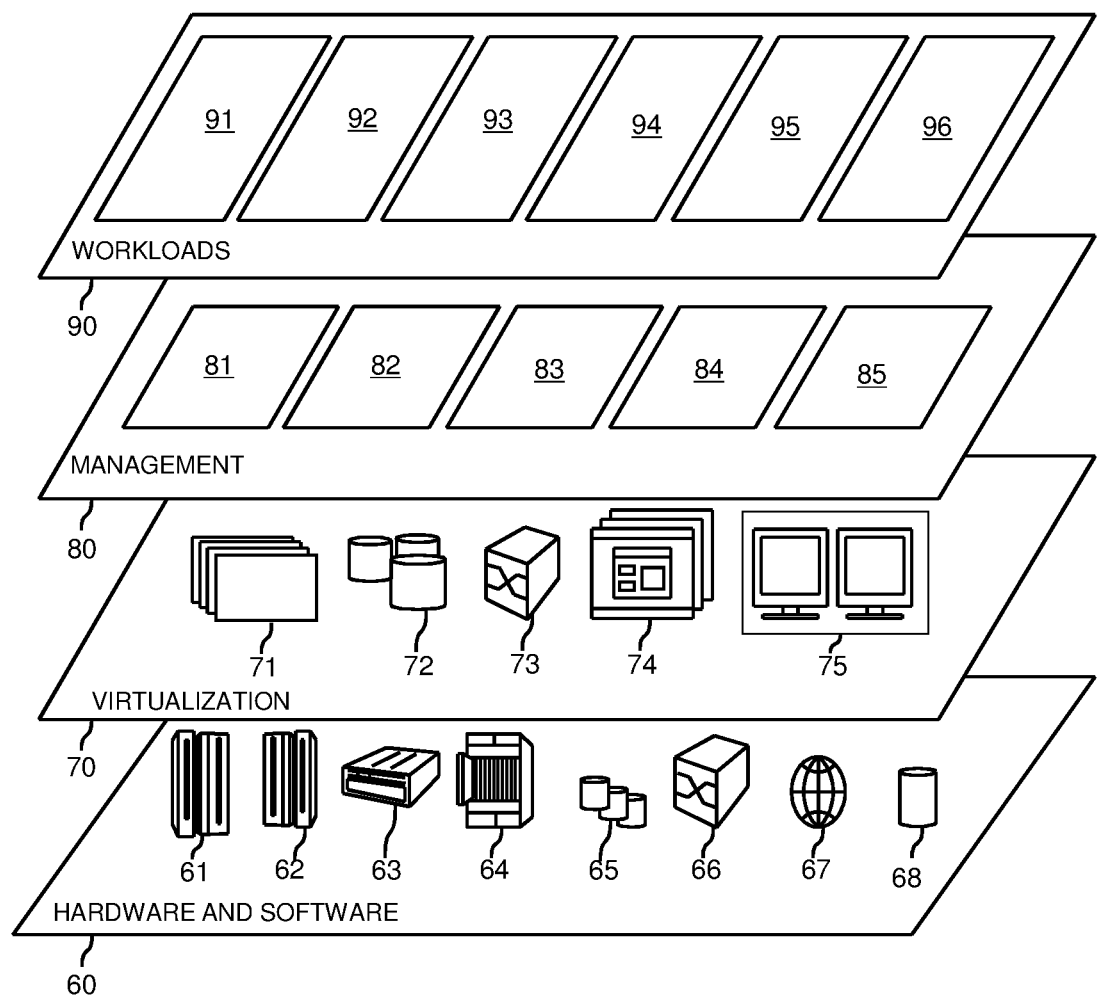
FIG. 13 illustrates a set of functional abstraction layers provided by cloud computing environment in one embodiment of the present disclosure.

Referring now to FIG. 13, a set of functional abstraction layers provided by cloud computing environment 50 (FIG. 12) is shown. It should be understood in advance that the components, layers, and functions shown in FIG. 13 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and machine learning and/or spectral clustering processing 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, run concurrently, substantially concurrently, in a partially or wholly temporally overlapping manner, or the blocks may sometimes be run in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. As used herein, the term "or" is an inclusive operator and can mean "and/or", unless the context explicitly or clearly indicates otherwise. It will be further understood that the terms "comprise", "comprises", "comprising", "include", "includes", "including", and/or "having," when used herein, can specify the presence of stated features, integers, steps, operations, elements, and/or components, but do not preclude the presence or addition of one or more other features, integers, steps, operations, elements, components, and/or groups thereof. As used herein, the phrase "in an embodiment" does not necessarily refer to the same embodiment, although it may. As used herein, the phrase "in one embodiment" does not necessarily refer to the same embodiment, although it may. As used herein, the phrase "in another embodiment" does not necessarily refer to a different embodiment, although it may. Further, embodiments and/or components of embodiments can be freely combined with each other unless they are mutually exclusive.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A machine learning system comprising:
a processor;
a memory device coupled with the processor;
a sensor coupled with the processor;
the processor configured at least to:
  receive data from the sensor;
  create graph Laplacian of the data and store in the memory device;
  compute spectral characteristic by applying density of states and detect spectral gaps in an unsupervised manner in the spectral characteristic to determine r number of clusters, r being a hyper-parameter for machine learning;
  compute a range space of a rational matrix of the graph Laplacian, r being determined based on dynamically increasing projection subspace for capturing eigenvalues, in which the subspace is built by computing the range space, and without requiring estimation of the eigenvalues located inside a disk in a complex plane;
  train an unsupervised machine learning model based on the hyper-parameter r to cluster the received data, wherein to train the unsupervised machine learning model, the processor is configured to perform K-means clustering on the range space of rational matrix of the graph Laplacian using r as the number of clusters, the K-means clustering trained to return r clusters of the received data;
  the data including computer network traffic data, wherein the unsupervised machine learning model is trained to classify the computer network traffic data into r clusters of security levels; and
  run the trained unsupervised machine learning model on incoming data traffic in real-time to detect a security level cluster to which the incoming data traffic belongs, and based on the security level cluster, filter the incoming data traffic to prevent unwanted data from entering a target computer system.

2. The system of claim 1, wherein the range space is computed using a trapezoidal rule.

3. A computer program product comprising a computer readable storage medium having program instructions embodied therewith, the program instructions readable by a device to cause the device to:
- receive data from the sensor;
- create graph Laplacian of the data and store in the memory device;
- compute spectral characteristic by applying density of states and detect spectral gaps in an unsupervised manner in the spectral characteristic to determine r number of clusters;
- compute range space of a rational matrix of the graph Laplacian, r being determined based on dynamically increasing projection subspace for capturing eigenvalues, in which the subspace is built by computing the range space, and without requiring estimation of the eigenvalues located inside a disk in a complex plane;
- train an unsupervised machine learning model based on the hyper-parameter r to cluster the received data, wherein to train the unsupervised machine learning model, the device is caused to perform K-means clustering on the range space of rational matrix of the graph Laplacian using r as the number of clusters, the K-means clustering trained to return r clusters of the received data;
- the data including computer network traffic data, wherein the unsupervised machine learning model is trained to classify the computer network traffic data into r clusters of security levels; and
- run the trained unsupervised machine learning model on incoming data traffic in real-time to detect a security level cluster to which the incoming data traffic belongs, and based on the security level cluster, filter the incoming data traffic to prevent unwanted data from entering a target computer system.

4. The computer program product of claim 3, wherein the range space is computed using a trapezoidal rule.

5. A computer-implemented machine learning method comprising:
- receiving data from the sensor;
- creating graph Laplacian of the data and store in the memory device;
- computing spectral characteristic by applying density of states and detect spectral gaps in an unsupervised manner in the spectral characteristic to determine r number of clusters, r being a hyper-parameter for machine learning;
- computing a range space of a rational matrix of the graph Laplacian, r being determined based on dynamically increasing projection subspace for capturing eigenvalues, in which the subspace is built by computing the range space, and without requiring estimation of the eigenvalues located inside a disk in a complex plane;
- training an unsupervised machine learning model based on the hyper-parameter r to cluster the received data, wherein to train the unsupervised machine learning model, the processor is configured to perform K-means clustering on the range space of rational matrix of the graph Laplacian using r as the number of clusters, the K-means clustering trained to return r clusters of the received data;
- the data including computer network traffic data, wherein the unsupervised machine learning model is trained to classify the computer network traffic data into r clusters of security levels;
- running the trained unsupervised machine learning model on incoming data traffic in real-time to detect a security level cluster to which the incoming data traffic belongs, and based on the security level cluster, filter the incoming data traffic to prevent unwanted data from entering a target computer system.

6. The method of claim 5, wherein the range space is computed using a trapezoidal rule.

\* \* \* \* \*